(12) United States Patent
Carson

(10) Patent No.: US 6,974,481 B1
(45) Date of Patent: Dec. 13, 2005

(54) TIBIAL TRIAL SYSTEM

(75) Inventor: Chris Carson, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 27 days.

(21) Appl. No.: 10/110,859

(22) PCT Filed: Oct. 20, 2000

(86) PCT No.: PCT/US00/28980

§ 371 (c)(1),
(2), (4) Date: Aug. 22, 2002

(87) PCT Pub. No.: WO01/28467

PCT Pub. Date: Apr. 26, 2001

Related U.S. Application Data

(60) Provisional application No. 60/160,532, filed on Oct. 20, 1999.

(51) Int. Cl.[7] .............................................. A61F 2/38
(52) U.S. Cl. ................... 623/20.14; 623/20.34
(58) Field of Search ..................... 623/20.14, 20.15, 623/20.21, 20.32, 20.33, 20.34, 18.11, 20.17; 606/68

(56) References Cited

U.S. PATENT DOCUMENTS

| | | | | |
|---|---|---|---|---|
| 5,246,459 A | * | 9/1993 | Elias ........................ | 623/20.34 |
| 5,290,313 A | * | 3/1994 | Heldreth ................... | 623/20.15 |
| 5,344,461 A | | 9/1994 | Phlipot | |
| 5,472,415 A | | 12/1995 | King et al. | |
| 5,522,897 A | | 6/1996 | King et al. | |
| 5,609,642 A | | 3/1997 | Johnson et al. | |
| 5,613,970 A | | 3/1997 | Houston et al. | |
| 5,683,469 A | * | 11/1997 | Johnson et al. .......... | 623/20.32 |
| 5,683,470 A | | 11/1997 | Johnson et al. | |
| 5,702,464 A | | 12/1997 | Lackey et al. | |
| 5,776,200 A | | 7/1998 | Johnson et al. | |
| 5,782,925 A | | 7/1998 | Collazo et al. | |
| 5,989,261 A | * | 11/1999 | Walker et al. ........... | 606/102 |

(Continued)

FOREIGN PATENT DOCUMENTS

| | | |
|---|---|---|
| EP | 0 780 093 A1 | 6/1997 |
| FR | 2 755 602 | 5/1998 |
| GB | 2 323 037 A | 9/1998 |

(Continued)

OTHER PUBLICATIONS

S&N Orthopaedics: Profix Total Knee System, one page, http://www.smithnephew.com/internet/products/knees/profix.html (Dec. 12, 1999).

(Continued)

*Primary Examiner*—Pedro Philogene
(74) *Attorney, Agent, or Firm*—Kilpatrick Stockton LLP

(57) ABSTRACT

The present invention provides a prosthetic trialing system for use in preparing a patient for an implant, and particularly, a tibial trialing system, as well as methods of using the trialing system to install the implant prostheses. Tibial trials according to the present invention employ intermediate stems or adapters (32) which connect to the plate trial (10). They therefore permit connection of the intermediate stem trial (32) to the trial plate (10) without interference to the proximal surface (12) of the plate trial (10) and without interference to the range of motion of a mobile bearing (62) on the plate trial (10). Additionally, a range of intermediate stem trials (32) and stems (52) may be offered to fit a range of plates (10) for various geometries and modularity.

38 Claims, 14 Drawing Sheets

U.S. PATENT DOCUMENTS

| | | | |
|---|---|---|---|
| 6,063,091 A | * | 5/2000 | Lombardo et al. ............. 606/88 |
| 6,102,954 A | * | 8/2000 | Albrektsson et al. .... 623/20.32 |
| 6,447,549 B1 | * | 9/2002 | Taft ........................ 623/20.15 |
| 6,506,216 B1 | * | 1/2003 | McCue et al. ........... 623/20.34 |

FOREIGN PATENT DOCUMENTS

| | | |
|---|---|---|
| WO | WO 96/25123 | 8/1996 |
| WO | WO 97/09939 | 3/1997 |
| WO | WO 97/30661 | 8/1997 |

OTHER PUBLICATIONS

S&N Orthopaedics: Genesis II Total Knee System, two pages, http://www.smithnephew.com/internet/products/knees/gen2.html (Oct. 12, 1999).

Augusta Orthopedic Surgery—Knee Procedures, six pages, http://www.augustaortho.com/knee.htm (Oct. 2, 1999).

* cited by examiner

Figure 33a
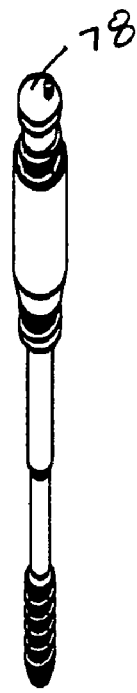
Figure 33b
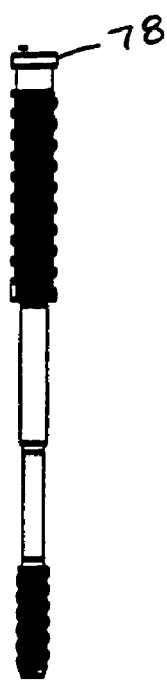
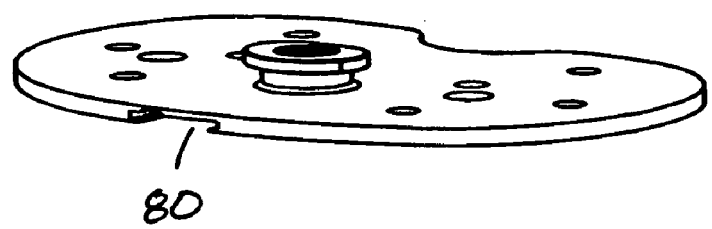
Figure 34
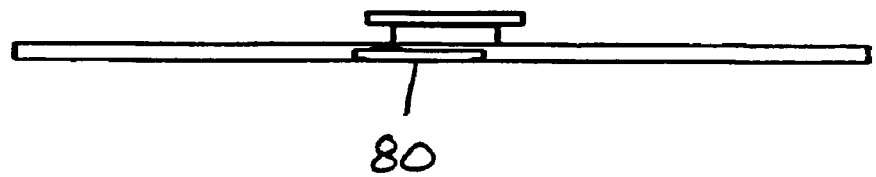
Figure 35

TIBIAL TRIAL SYSTEM

CROSS-REFERENCE TO RELATED APPLICATIONS

This application claims priority to U.S. Provisional Application No. 60/160,532 filed on Oct. 20, 1999 and International Application No. PCT/US00/28980 filed on Oct. 20, 2000 and published in English as International Publication No. WO 01/28467 A1 on Apr. 26, 2001, the entire contents of each are incorporated herein.

FIELD OF THE INVENTION

The present invention relates to a tibial trialing system for use in preparing a patient's tibia, as well as methods of using the trialing system to install the implant prostheses.

BACKGROUND

In knee joint replacement surgery, a surgeon typically affixes two prosthetic components to the patient's bone structure; a first to the patient's femur and a second to the patient's tibia. These components are typically known as the femoral component and the tibial component respectively.

The femoral component is placed on a patient's distal femur after appropriate resection. One common type of femoral component features a J-shaped cross section. The femoral component is usually metallic, having a highly polished outer condylar articulating surface.

A common type of tibial component uses a tray or plate that generally conforms to the patient's resected proximal tibia. The tibial component also usually includes a stem which extends generally perpendicular to the plate in order to extend into a surgically formed opening in the patient's intramedullary canal.

A plastic or polymeric (often high density polyethylene or HDPE) insert or bearing fits between the plate of the tibial component and the femoral component. This insert or bearing provides a surface against which the femoral component condylar portion articulates (moves in gross motion corresponding generally to the motion of the femur relative to the tibia).

In so-called mobile bearing knee prostheses, the bearing also engages in motion relative to the plate. Such motion can be translational and/or rotational sliding motion relative to the plate. In other types of mobile bearing knee prostheses, the bearing can engage in other types of motion relative to the plate and/or femoral component.

Portions of the tibial and femoral components may be at least partially porous coated, or they may be non-porous coated. Porous coating surfaces of implant components promote bone ingrowth, which supplants the need for some or all of the cement typically employed with non-porous coated implant components.

Accurately positioning and fitting the prosthetic components is of paramount interest to the surgeon and to the patient for a number of reasons. Each patient has a different bone structure and geometry, as a static matter. Dynamically, motion of the tibia relative to the femur about every axis varies from one patient to the next. Even though the surgeon uses various imaging techniques and palpation to study a particular patient's anatomy, she nevertheless gains considerable additional information required to fit the prosthetic components after the knee has been surgically exposed and she begins the surgery.

This diversity of knee structure, geometry and dynamics compels most suppliers of prosthetic components to offer a wide range of prosthetic options for knee replacement surgeries. These include, for instance, femoral and tibial components for primary surgeries as well as revision surgeries, porous coated and non-porous coated components, various sizes of stems for various tibial component plates, various femoral component interfaces for primary and revision cases, and prostheses which feature mobile bearings as well as those which do not. The present invention is intended for use with any of these options.

So-called trial prostheses are conventional for, among other things, trying the fit of prosthesis or implant components to respective portions of the joint. After shaping the femur and the tibia, the surgeon may temporarily fit trial components instead of the actual prosthetic components to the femur and/or tibia respectively. This enables the surgeon to test the fit of the components to the femur and tibia and to test their performance both statically and dynamically throughout a desired range of motion. Use of trial prosthetics instead of the actual implants also allows the surgeon to perform this testing and achieve a more perfect fit and a more accurate performance of the actual component without introducing a number of "new" actual prosthetic components into the surgical field.

Using actual prosthetic components for this fitting procedure is undesirable for a number of obvious reasons. For example, the trial prosthetic components allow the surgeon to position, move, and fit components while trying various sizes and, if desired, while modifying bone structure, without imparting wear and tear on actual prosthetic components, upon which destruction could have adverse long-term effects.

Modularity serves many interests in implant prosthetics as well as trial prosthetics. For instance, a particular tibial plate may accommodate a range of sizes and angles of stems which fit to the plate via a Morse taper. The surgeon thus has a range of options available without subjecting the patient or the organization to the expense of a separate entire tibial component corresponding to each option. Similarly, it is desirable in tibial trial prosthetics to employ the notion of modularity. Thus, it is preferable in many cases to offer a tibial trial component which features a base plate and a number of stems of varying lengths and perhaps varying angles which are adapted to couple or connect to the plate in order to correspond to a range of sizes and configurations of actual tibial components. U.S. Pat. Nos. 5,609,642, 5,683,469, 5,683,470, and 5,776,200 to Johnson, et al., which are incorporated herein by this reference, disclose tibial trial components which are modular in nature. These patents disclose, among other things, a tibial trial prosthesis which include a plate that attaches to a trial stem using a trial taper and a trial stem coupler. The taper receives the coupler and thereby the stem, and it fits to the plate via a component such as a bushing, which is inserted through the top or proximal surface of the plate.

Tibial plate design can impose constraints on how the stem trial is connected to the plate trial. Plates, both implant and trial, can be relatively thin, and they are often not totally flat or planar in structure. For example, many non-porous tibial plates, and their corresponding trial plates, include fins that extend from the distal surface into the tibia for rotational stability. Additionally, tibial plates which receive mobile bearings include a post such as a T-post which extends from the proximal surface of the plate in order to retain and restrain the mobile bearing to certain degrees of freedom and range of motion. The post structure and other structures on either surface of the plate can occupy the space on or within the plate through which a member for retaining the stem would be inserted through the proximal surface. Additionally, such a proximal surface-inserted member could interfere with insertion of devices for forming the tibia to receive the fins. It may also interfere with movement of the bearing or insert relative to the plate in a mobile bearing design. Accordingly, not all tibial trial components are well-suited for the sort of modular approach disclosed in the above-referenced Johnson, et al. patents.

In one commercial offering, for example, the tibial base plate of a mobile bearing system includes a T-post and a tapered stem. The non-porous tibial base plate also includes fins for rotational stability. A simple technique and instrumentation system is required to trial the tibial base plate and to prepare the proximal tibia for the stem and the fins. (Again, the present invention is not limited to use with tibial plates that include T-post and fins, but may be used with any plate.) The bone cannot be prepared for fins through the tibial trial plate when the position of the T-post interferes with current punching techniques.

SUMMARY OF THE INVENTION

Tibial trials according to the present invention employ intermediate stem trials, also referred to as "adapters," which connect to the plate trial without the need for insertion of any components through the proximal surface of the plate trial. They therefore permit connection of the intermediate stem trial to the plate trial without interference to the T-post on the proximal surface of the plate trial in mobile bearing knees. They also permit connection of the intermediate stem trial to the plate trial without interference to the range of motion of a mobile bearing on the plate trial. Additionally, a range of intermediate stem trials and stems may be offered to fit a range of plates for various geometries and modularity. (The terms "intermediate stem," "intermediate stem trial," "adapter," and "trial adapter" for the purpose of this document mean a connector or intermediate stem that cooperates with, can be coupled to or that interfaces with a bottom portion of a prosthetic plate, such as a tibial plate.)

According to the present invention there is provided a prosthetic trial apparatus for use in preparing a patient for an implant, the trial apparatus comprising:
 (a) a plate having a top surface and a bottom surface, the bottom surface containing a plate interface; and
 (b) a trial adapter having a proximal end and a distal end and having
   (i) a first adapter interface at its proximal end adapted to connect to the plate interface in a manner that does not interfere with the top surface of the plate and that provides a secure connection of the adapter to the plate; and
   (ii) a second adapter interface at its distal end.

There is also provided a tibial trial prosthesis, comprising a tibial trial plate having first and second sides and an intermediate stem trial adapted to connect to the first side of the tibial trial plate in a manner that does not interfere with the second side of the tibial trial plate. More particularly, there is provided tibial trial apparatus for use in preparing a patient for an implant, the tibial trial apparatus comprising:
 (a) a tibial trial plate having a top surface and a bottom surface, the bottom surface containing a plate interface; and
 (b) an trial adapter having a proximal end and a distal end and having
   (i) a first adapter interface at its proximal end adapted to connect to the tibial plate interface in a manner that does not interfere with the top surface of the plate and that provides a secure connection of the adapter to the plate; and
   (ii) a second adapter interface at its distal end. The tibial trial apparatus may also have a trial stem adapted to connect to the second adapter interface. In one embodiment, the plate interface is a cavity, with the adapter interface fitting into the cavity. In another embodiment, the plate interface is a projection from the bottom surface, with the adapter interface received in projection.

Tibial trial prosthesis kits are also provided, having
 (a) a plurality of plates having a range of shapes, each plate having a top surface and a bottom surface, the bottom surface containing a plate interface;
 (b) a plurality of trial stems having a range of various lengths, angles, and widths, each trial stem adapted to be inserted into the intramedullary canal of a patient's bone; and
 (c) a plurality of adapters having a range of various angles to fit range of plates for various geometries and modularity, each adapter having a proximal end and a distal end and including:
   (i) a first adapter interface at its proximal end adapted to connect to the plate interface in a manner that does not interfere with the top surface of the plate and that provides a secure connection of the adapter to the plate; and
   (ii) a second adapter interface at its distal end adapted to connect to the trial stem. Methods for replacing a knee joint using the trial apparatus of the present invention are also provided.

According to one narrower embodiment of the present invention, the tibial plate trial is a generally flat plate with a peripheral shape that matches the tibial plate implant. The plate features a number of holes or openings whose locations are coincident to the locations of spikes found on the distal surface of the tibial plate implant. The holes are used to guide a punch or drill which prepares the proximal tibia for implantation of the tibial plate implant spikes. Two small integral spikes on the distal surface of the tibial plate trial secure the position of the tibial plate trial until headed pins are inserted. Two holes are counter-bored to accept the headed pins in order to secure the tibial plate trial firmly to the proximal tibia during trial reduction. The depth of the counter-bore allows the heads of the pins to be recessed below the proximal surface of the tibial plate trial in order to prevent impingement of the trial insert or bearing. The two counter-bored holes are positioned so that only one porous and one non-porous punch guide is needed for each size tibial component. This can be significant when the stem is not positioned in the center of the plate, but rather is offset medially at certain distances on various sizes and styles of tibial components, both left and right.

The tibial plate trial in this mobile bearing embodiment of the invention also has a T-post on the proximal surface which in turn features an internal thread to accept a trial rotation peg. A through hole is formed in the center of the threads to allow for cleaning biologic debris from the threadform. The T-post receives a trial insert or bearing to accomplish trial reduction. The addition of a trial rotation peg may change the motion of the articular insert trial from rotation and translation to rotation only.

Once the appropriate plate trial has been selected, it can be coupled to an intermediate stem trial or adapter. An advantage of the present invention is that this coupling is accomplished without the need for components to be inserted through the proximal surface of the plate trial. The coupling can occur either on the distal surface of the plate trial or within the plate trial, without interfering with the proximal surface of the plate trial. There are numerous suitable coupling mechanisms that may be used with this invention. Some examples include a slot or mating groove on the plate trial that may receive a corresponding connecting portion of an intermediate stem trial; an opening or hole on the plate trial that receives a corresponding connecting portion of the intermediate stem trial; a projection from the distal surface of the plate trial that is adapted to receive a corresponding connecting portion of an intermediate stem trial; or any other structure associated with coupling, such as a collar, a ball and detent mechanism, a bayonet fitting, a Morse taper, magnetic surfaces, or the like.

For instance, a slot or mating groove may be located on the distal surface of the plate trial. The slot extends preferably from an edge of the plate to the location corresponding to the attachment of the stem to the plate on the actual implant. An alignment groove may be located within the distal surface parallel to the slot and terminates appropriately.

The slot may reflect any shape that can receive a corresponding connecting portion. For instance, the connecting portion may be a dovetail slot that is oriented to receive a chamfered flange component. The slot could also comprise a half-round mating groove or a T-slot mating groove, oriented to receive a corresponding connecting portion.

The intermediate stem trial may be a generally elongated or cylindrical structure which features a connecting portion on the proximal end that is received into the slot of the tibial plate trial. The connecting portion on the proximal end corresponds to the shape of the slot located on the distal surface of the plate trial. In one embodiment, the connecting portion is a chamfered flange that has two parallel edges which help reduce rotational toggle between the intermediate stem trial and the tibial plate trial.

A small boss may be located on the proximal surface of the intermediate stem trial. This boss is positioned to restrain rotation of the intermediate stem trial relative to the plate trial, and to orient the intermediate stem trial about its longitudinal axis relative to the plate trial. The boss thus allows an angled intermediate stem trial to be connected to the tibial plate trial so that the angle points in the posterior (or other desired) direction.

The intermediate stem trial may also feature an additional connecting mechanism to secure its attachment to the plate trial. The connecting mechanism may be a hole and detent mechanism located on the proximal surface of the intermediate stem trial. In this embodiment, the plate trial features a small recess on its distal surface in order to receive the connecting mechanism.

Alternatively, the plate trial and intermediate stem may be attached without the use of a slot or mating groove. The plate trial may be slotless, and connection between the plate trial and the intermediate stem trial may be accomplished by a locking mechanism, in lieu of a mating groove. The intermediate stem trial may have a hole and detent mechanism at its proximal surface that releases and locks within a recess in an opening on the plate trial.

A threadform may be located inferior to the connecting portion of the intermediate trial stem (such as a chamfered flange) and receives a threaded collar. The collar may be tightened against the tibial plate trial to secure the intermediate stem trial to the plate trial. The collar features a narrowed circumference to improve gripping strength during tightening.

Another threadform is located on the distal end of the intermediate stem trial coaxially with the proximal threadform or angled relative to the axis of the threadform in order to correspond to or mimic stem geometry of actual implants. The distal threads of the intermediate stem trial are configured to accommodate stem trials.

Porous and non-porous punch guides used in connection with the trial components have two distal spikes which are coincident to the two counter-bored holes of the tibial base plate trial. Both punch guides have slots to accept a punch that prepares for the distal geometry of their respective implant and recesses to accept a quick connect handle. The slot in the non-porous punch guide is designed to accept several, preferably four, different sizes of fin punches.

Interfaces other than a slot or opening that may receive a corresponding connecting portion may be employed to connect or secure the tibial plate trial and the intermediate stem trial, including any conventional structure or configuration. Any structure associated with coupling, such as a collar, a ball and detent mechanism, a bayonet fitting, a Morse taper, magnetic surfaces, or any other desired connection, structure or geometry can be used. Conventional features other than threaded collars or spring action ball bearings or plungers may be used to secure the intermediate stem trial to the tibial plate trial. Conventional features other than a threadform could be used to attach a stem trial to the intermediate stem trial. Conventional features other than a boss could be used to orient the intermediate stem trial in the correct position on the plate trial. Conventional features other than a T-post on the tibial plate trial may be used to accommodate the trial insert or bearing.

One advantageous feature of this design is that the surgeon has the option of not using the stem trial. Most mobile bearing tibial trials either have a stem trial that requires some tibial preparation or they have two tibial trials, one with a stem and one without. By not using a stem, the surgeon has not committed herself to use a mobile bearing device. After performing a trial range of motion, if the surgeon is not satisfied with the function of the knee, she may switch to a fixed bearing device, which may require a different tibial preparation than the mobile bearing device. Even with a fixed bearing device, surgeons sometimes complain about having to perform tibial preparation before using the tibial trial. This embodiment addresses that shortcoming by accommodating both stemmed and stemless tibial trials.

It is therefore an object of the present invention to provide enhanced modularity in prosthetic trials, and more particularly in tibial trials.

It is an additional object of the present invention to provide tibial trials with enhanced modularity and without the need for attachment of stem components via components which must be inserted through the proximal surface of the tibial plate trial.

It is an additional object of the present invention to provide tibial trials with enhanced modularity in order to accommodate modular bearing tibial trials and other implant trials where structure would otherwise interfere with conventional modularity structure or techniques.

Other objects, features and advantages will become apparent with respect to the remainder of this document.

BRIEF DESCRIPTION OF THE DRAWINGS

FIG. 29b is a side view of FIG. 29a.

FIG. 30b is a side view of FIG. 30a.

FIG. 33a is a perspective view of an alternate embodiment of an intermediate stem trial that has a T-slot connecting portion.

FIG. 33b is a side view of FIG. 33a.

FIG. 34 is an anterior perspective view of a plate trial having a T-slot mating groove for use with the intermediate stem trial of FIGS. 33a and 33b.

FIG. 35 is an anterior elevation view of the plate trial of FIG. 34.

DETAILED DESCRIPTION OF THE DRAWINGS

Figure 1:
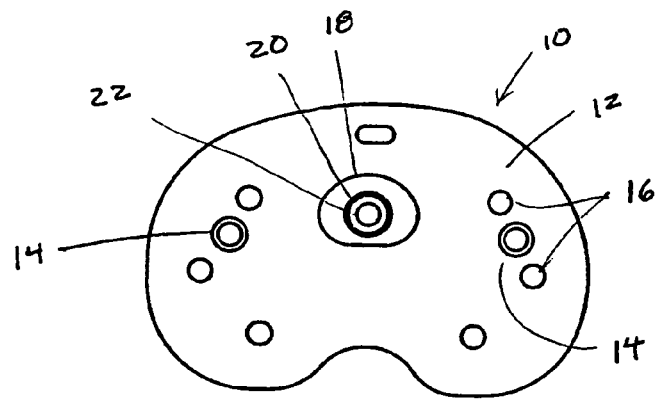
FIG. 1 is a top plan view of a tibial plate trial according to a preferred embodiment of the present invention, which shows generally the proximal surface of the plate trial.
Figure 6:
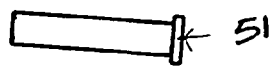
FIG. 6 shows a side elevational view of a bone pin according to a preferred embodiment of the present invention, which fits with plate trials shown in FIGS. 1–3.

FIG. 1 is a top plan view of a preferred embodiment of a tibial plate trial 10 according to a preferred embodiment of the present invention. FIG. 1 shows generally, the proximal surface 12 of the plate trial. The trial 10 may be formed of any desired material, but is preferably any conventional metallic material. Proximal surface 12 of plate trial 10 may be generally flat or planar to receive an insert trial. In any event, the shape and configuration of plate trial 10 generally matches the shape and configuration of the actual implant to which it corresponds. A pair of openings 14 may be formed in plate 10 to accommodate bone pins as shown in FIG. 6 in order for positioning plate 10 on the resected tibial portion. A number of guide openings 16 may be formed in plate 10 to act as drill or punch guides for further preparation of the tibial portion.

Figure 3:
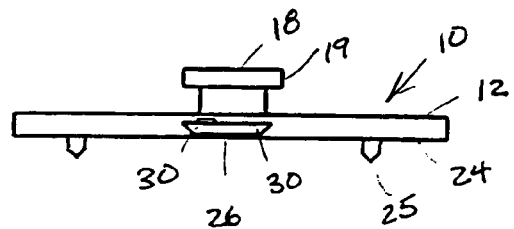
FIG. 3 is an anterior elevational view of the plate trial of FIG. 3, which shows generally the T-post extending from the proximal surface of the plate trial.
Figure 13:
FIG. 13 is a side elevational view of a preferred embodiment of a rotation peg which fits with the plate trial of FIGS. 1–3.
Figure 14:
FIG. 14 is a top plan view of the rotation peg of FIG. 13.

The proximal surface of plate trial 10, which is used in connection with implantation of a mobile bearing prosthesis, contains a T-post 18 which extends in the proximal direction generally vertically from proximal surface 12 of plate trial 10. As shown in FIG. 3, T-post 18 contains a flange 19 which is adapted to retain an insert trial against plate trial 10 in sliding (rotational and/or translational) relationship. T-post 18 also includes a threaded bore 20 with a through hole 22. The threaded bore 20 accepts a trial rotation peg as shown in FIGS. 13 and 14 for further restraint of the insert trial on the plate trial 10. The through hole 22 permits removal of debris from threaded bore 20.

Figure 2:
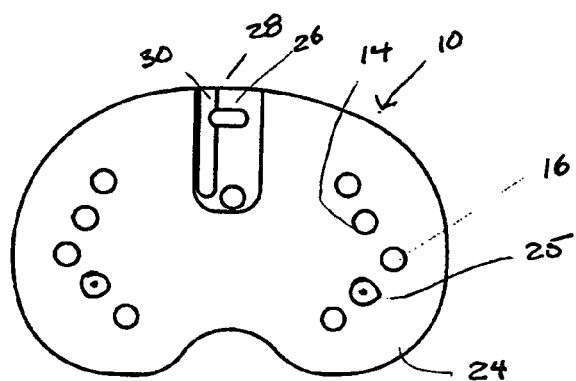
FIG. 2 is a bottom plan view of the plate trial of FIG. 1, which shows generally the distal surface of the plate trial.

FIG. 2 is a bottom plan view of the plate trial 10 of FIG. 1 which shows the distal surface 24 of plate trial 10. Holes 14 and 16 may be seen. Small spikes 25 may extend from distal surface 24 to locate plate trial 10 on the tibia.

As previously mentioned, one of the advantages of the present invention is that the coupling of the plate trial 10 and the intermediate stem may be accomplished without the need for components to be inserted through the proximal surface of the plate trial. The coupling can occur on the distal surface 24 of the plate trial or within the plate trial, without interfering with the proximal surface of the plate trial. There are numerous suitable coupling mechanisms that may be used with this invention. Any structure associated with coupling, such as a slot and connecting portion, a collar, a ball and detent mechanism, a bayonet fitting, a Morse taper, magnetic surfaces, or the like are all encompassed by the present invention. The figures that follow provide possible examples, but are not intended to be limiting.

Figure 5:
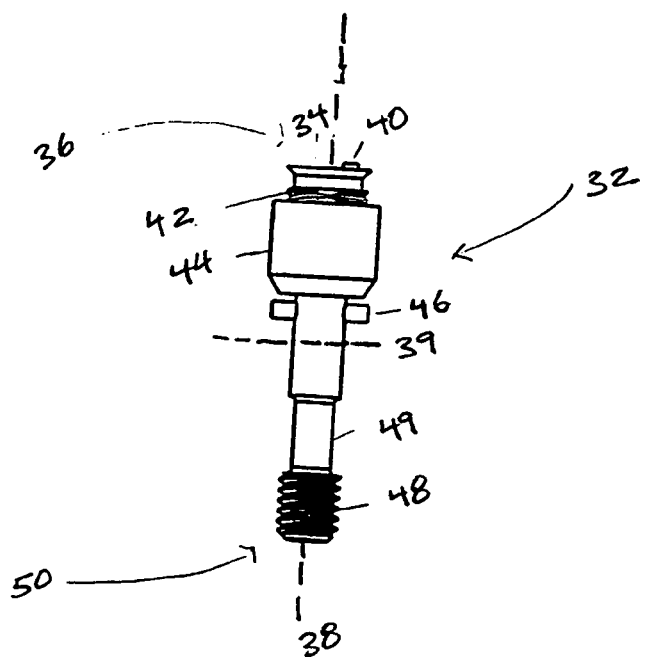
FIG. 5 is a rear elevational view of a preferred embodiment of an intermediate stem trial according to the present invention, which fits with the plate trial shown in FIGS. 1–3.

In one embodiment, a dovetail slot 26 is formed in distal surface 24 to receive the proximal end of an intermediate stem trial as shown in FIG. 5. Slot 26 may be formed as shown in FIGS. 2 and 3 or as otherwise desired. It need not be dovetail but could have a T-shaped cross section or be formed or configured as otherwise desired in length, width and cross section. In the preferred embodiment as shown in FIGS. 1–3, slot 26 extends from anterior edge 28 of plate trial 10. An alignment groove 30 is formed in slot 26 and terminates as desired for use in maintaining proper orientation of an intermediate stem trial relative to plate trial 10.

Figure 4:
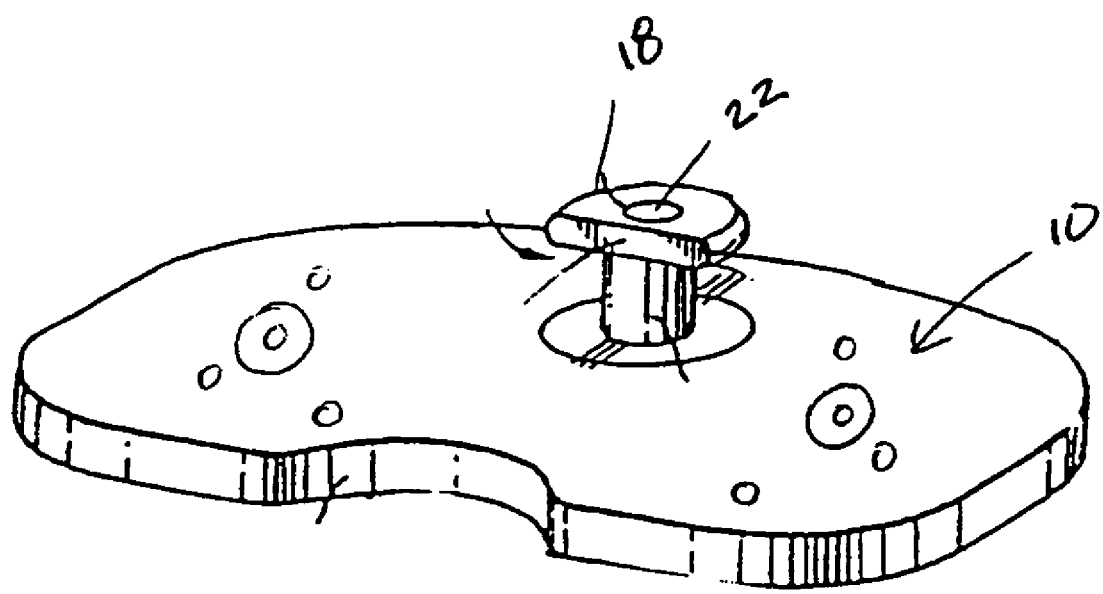
FIG. 4 is a perspective view of a second embodiment of a tibial plate trial according to the present invention.

FIG. 4 shows a second embodiment of a plate trial 10 according to the present invention.

FIG. 5 shows an intermediate stem trial 32 for use in connection with plate trial 10. Intermediate stem trial 32 is generally longitudinal in shape and features a chamfered flange 34 at proximal end 36 for cooperation with dovetail slot 26 in plate trial 10. A boss 40 may be positioned on the proximal end 36 of intermediate stem trial 32 in order to cooperate with alignment groove 30 in slot 26 of plate trial 10. Intermediate stem trial 32 is thereby oriented about its longitudinal axis 38 relative to plate trial 10. This is particularly useful where an angle is formed in stem trial 32 to mimic angles in implant stems. Such an angle may be formed, for instance, about axis 39. Angles may be, for instance, three degrees or four degrees.

In the preferred embodiment, various intermediate stem trials of various lengths and angles may be provided in order to correspond to narrow or wide ranges of tibial implants as desired.

A threaded surface 42 is formed near the proximal end 36 of intermediate stem trial 32 in order to accept a rotational collar 44. Collar 44 may be rotated on the thread form 42 for biasing against the distal surface 24 of tibial plate trial 10 in order to tension the chamfered flange 34 in the dovetail slot and thus secure the intermediate stem trial 32 to the plate trial 10. Any desired stopping mechanism such as a pin 46 may be employed to prevent collar 44 from becoming separated from intermediate stem trial 32.

At or near the distal end 50 of intermediate stem trial 32 may be found a second threaded surface 48. Threaded surface 48 is formed on a shank 49 which may be coaxial to the remainder of intermediate stem trial 32 so that threadforms 48 and 42 are coaxial about longitudinal axis 38. In intermediate stem trials 32 which are angulated, longitudinal axis 38 is "bent" at axis 39 or as otherwise desired to cause shank 49 to be angulated relative to the proximal portions of intermediate stem trial 32. In preferred embodiments of the present invention, axis 38 may be "bent" 3 degrees or 4 degrees, for instance, to accommodate implant stems which contain 3 or 4 degree angles. Stem trial 32 may be provided in various lengths and angles for desired modularity.

FIG. 6 shows a bone pin 51 which is received in openings 14 of the plate trial 10 shown in FIGS. 1–3. The bone pin 51 further secures the plate trial 10 to the proximal tibia.

Figure 7:
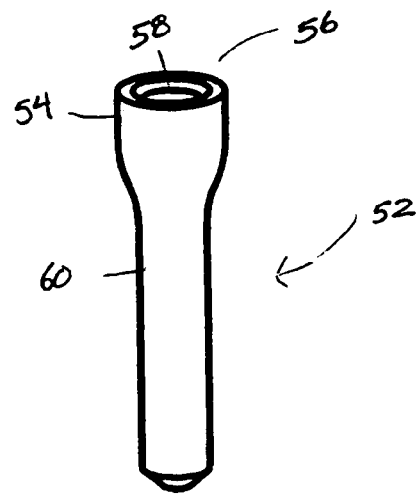
FIG. 7 is a perspective view of a stem trial according to a preferred embodiment of the present invention, which fits with the intermediate stem trial of FIG. 5.

FIG. 7 shows a stem trial 52 for use with intermediate stem trial 32 shown in FIG. 5. Connection portion 54 is formed in the proximal end of stem trial 52 for connection to the intermediate stem trial 32. In the embodiment shown in FIGS. 5 and 7, stem trial 52 is connected to intermediate stem trial 32 via a threaded bore 58 formed in proximal end 56 which cooperates with threads 48 on the distal end of intermediate stem trial 32. Any other connection device may be used. Elongated portion 60 forms the remainder of the stem trial 52. Various sizes, lengths and configurations of stem trial 52 may be connected to various sizes, lengths and configurations of intermediate stem trial 32 which may in turn be connected to various styles and configurations of plate 10 (if desired) in order to provide, in a modular fashion, a number of options for tibial trials which mimic the shape and configuration of actual tibial implant components with a minimal number of trial components.

Figure 8:
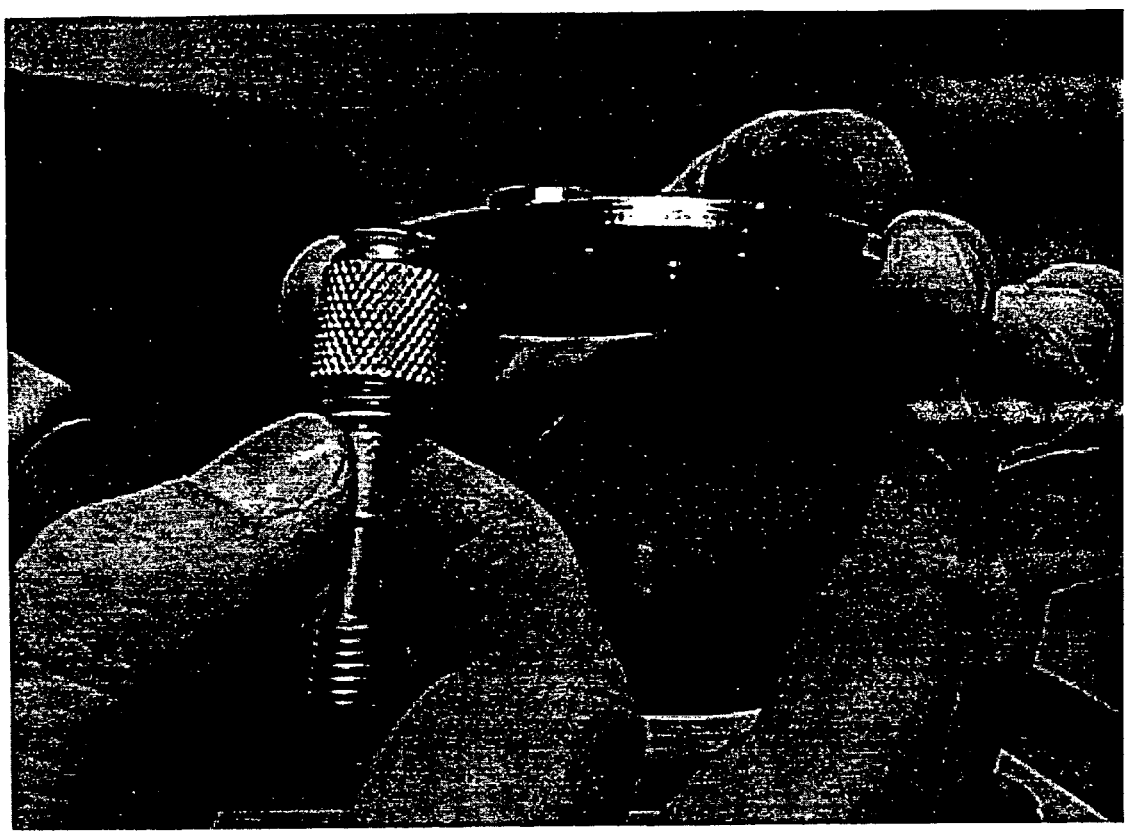
FIG. 8 is a perspective view of a plate trial as shown in FIGS. 1–3 being fitted to an intermediate stem trial as shown in FIG. 5.
Figure 9:
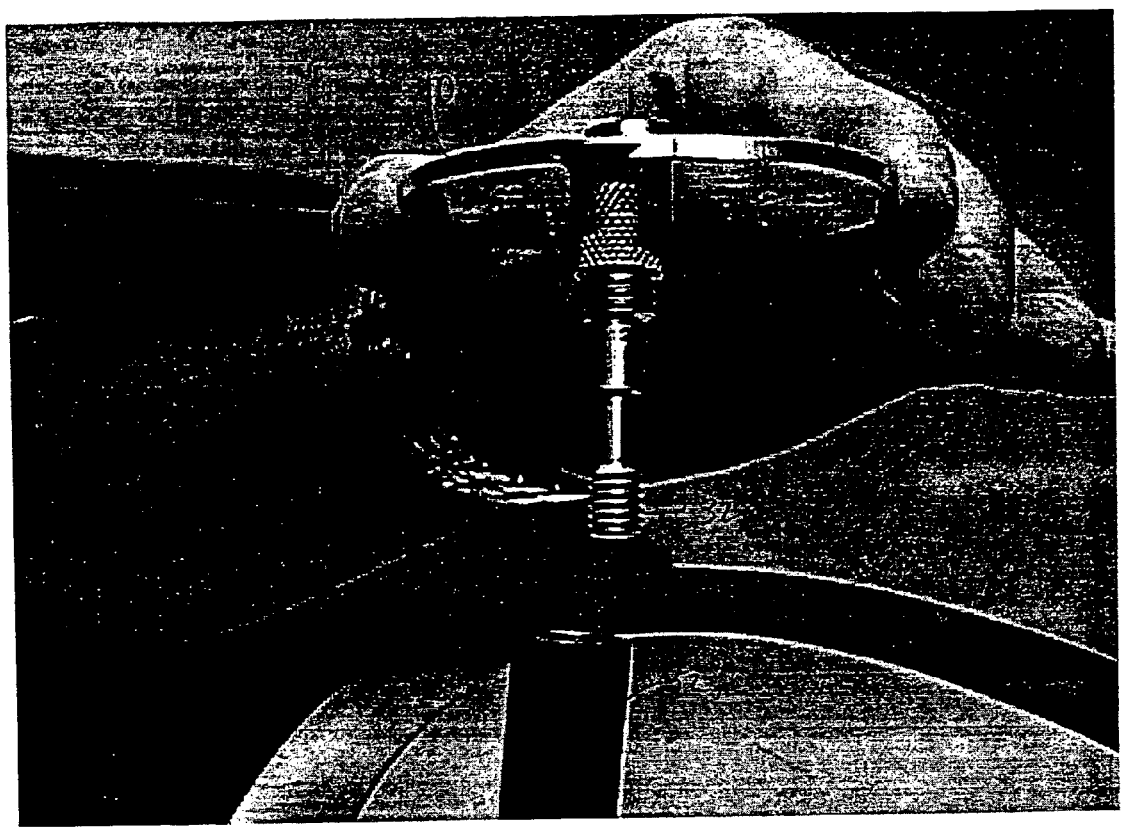
FIG. 9 shows the plate and intermediate stem trial of FIG. 8 being fitted to a stem trial.

FIG. 8 shows an intermediate stem trial 32 being inserted into the dovetail slot 26 of plate trial 10. FIG. 9 shows the intermediate stem trial 32 connected to plate trial 10 and ready for connection to stem trial 52.

Figure 10:
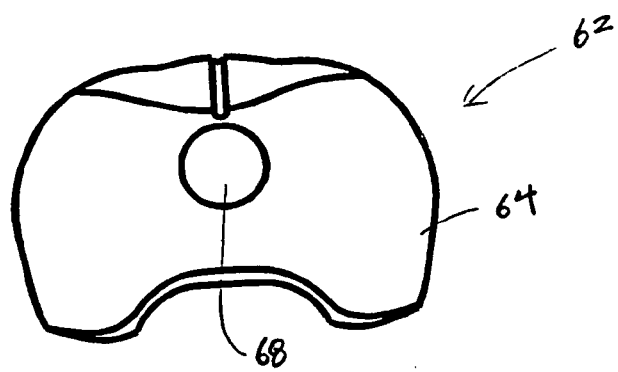
FIG. 10 is a top plan view of an insert or bearing trial according to a preferred embodiment of the present invention, which fits with the plate trial shown in FIGS. 1–3.
Figure 11:
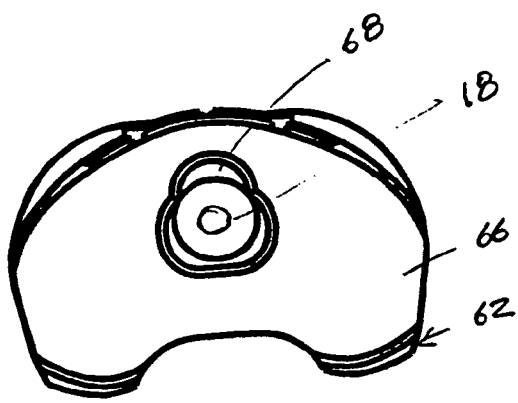
FIG. 11 is a bottom plan view of the insert trial of FIG. 10.
Figure 12:
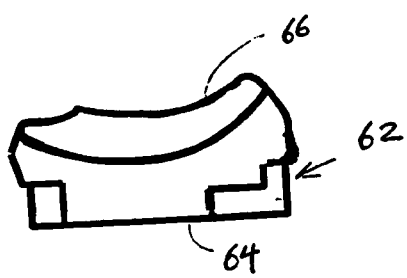
FIG. 12 is a side elevational view of the insert trial of FIGS. 10 and 11.

FIGS. 10–12 show an insert trial according to a preferred embodiment of the present invention which fits with plate 10 as shown in FIGS. 1–3. Insert trial 62 features a proximal surface 64, a distal surface 66, and an opening 68 which receives the T-post 18 of plate trial 10 in order to restrain and retain insert trial 62 so that its distal surface 66 slides translationally and/or rotationally with respect to proximal surface 12 of plate trial 10. Insert trial 62 corresponds to conventional modular bearings in conventional modular bearing implants. Thus, proximal surface 64 features concavities which receive portions of the femoral prosthesis.

FIGS. 13 and 14 show a rotation peg 70 which is received in the threaded bore 20 of T-post 18 of plate trial 10 in order further to retain insert trial 62 relative to plate trial 10.

Figure 15:
FIGS. 15–28 are perspective views which show a clinical surgical technique that can employ tibial trials according to the present invention.
Figure 16:
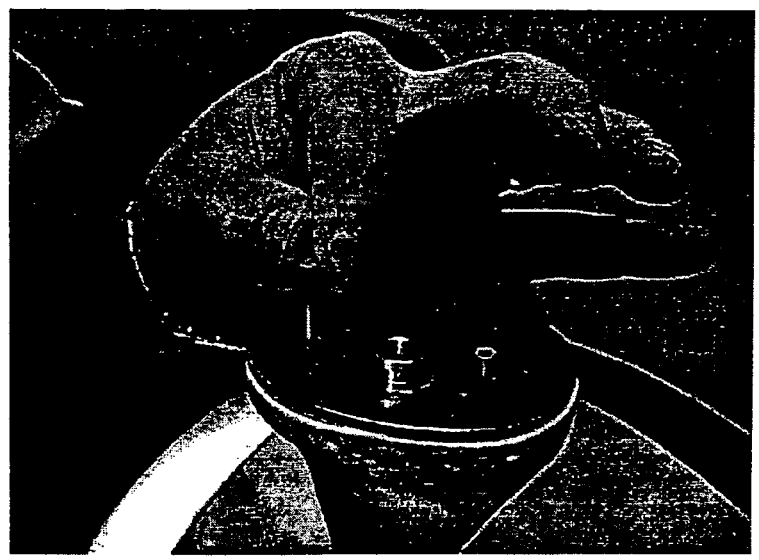

FIGS. 15–28 shows steps in a process for inserting a knee prosthesis. FIGS. 15–28 show such a process without use of the intermediate stem trial and stem trial. FIGS. 8 and 9 add those components into the process. In such a process, the femur and the tibia are resected to a shape and configuration which accepts, as nearly as possible, correctly dimensioned implant components. The actual or a trial femoral component may be placed on the femur. As shown in FIG. 15, a plate trial 10 according to the present invention is placed on the resected proximal tibia. FIG. 16 shows bone spikes 51 being placed into two recessed bone spike holes of plate trial 10. The heads of the bone spikes can be positioned below the proximal surface of the plate trial 10. Holes 16 can be used as drill or punch guides to prepare for spikes on a porous tibial plate.

Figure 17:

FIG. 17 shows an insert holder being used to place the insert trial 62 on plate trial 10. Obviously, the size of the insert trial 62 must match the size of the femoral component and plate trial 10.

Figure 18:
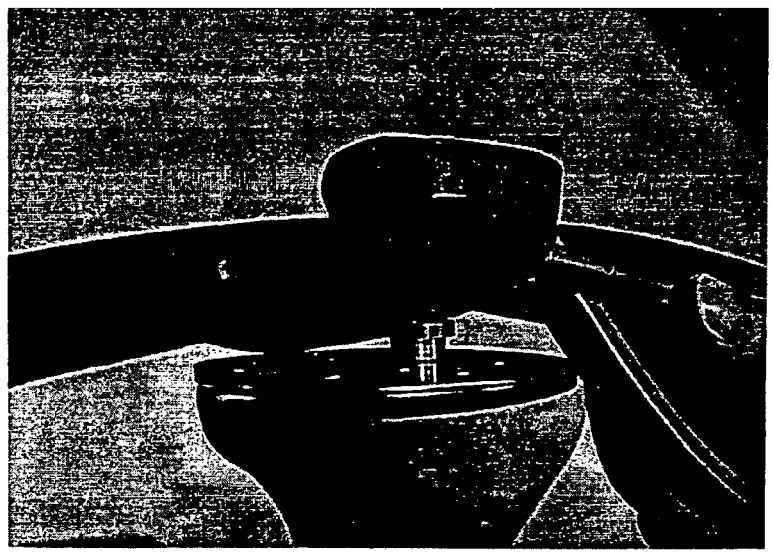

FIG. 18 shows the posterior positioned cross slot of the insert trial fitting over the T-post 18 of plate trial 10. This allows the opening in the insert trial 62 to engage the T-post 18 of plate trial 10.

Figure 19:
Figure 20:

FIG. 19 shows a rotation peg 70 being inserted into T-post 18. A rotation peg is optional and does not have to be used. FIG. 20 shows a trial range of motion performed to assess knee function and ligament balancing. The femoral component can be seen on the distal portion of the femur.

Figure 21:
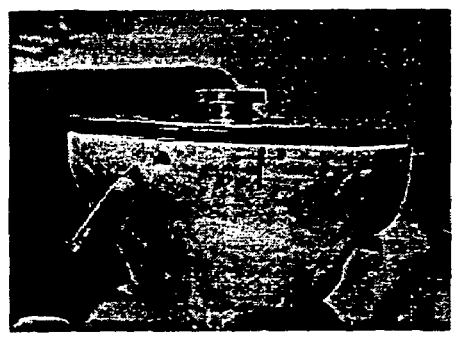

FIG. 21 shows that after tibial rotation alignment has been determined, a cautery pin or methylene blue dye can be used to mark the tibia relative to indicia on the anterior surface of plate trial 10.

Figure 22:
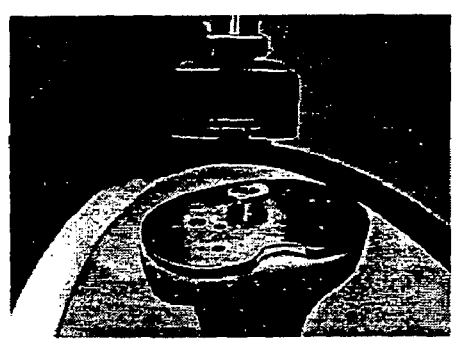

FIG. 22 shows an extractor being used to extract the plate trial 10.

Figure 23:
Figure 24:

A non-porous punch guide is used as shown in FIG. 23 for punching the proximal tibia to accommodate fins of finned implant plates. It is also possible for alternate embodiments of this invention to use a porous punch guide. The punch guide is aligned using the holes formed by bone spikes 51. As shown in FIG. 24, a thin punch is inserted through the punch guide into the proximal tibia to prepare it for non-porous (or alternatively, porous) implant fins and stem.

Figure 25:
Figure 26:
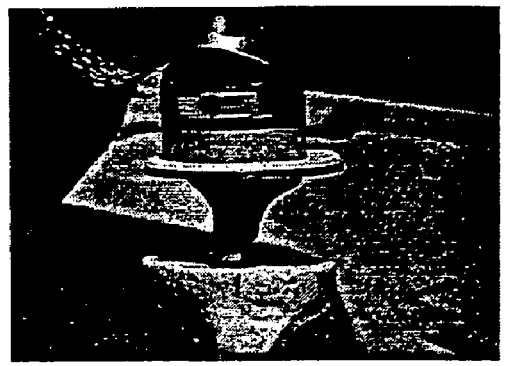
Figure 27:

FIG. 25 shows that after the punch guide has been removed, the actual tibial implant is secured with an impactor. FIG. 26 shows the non-porous tibial plate being impacted into the tibia until the distal surface of the plate is flush with the resected tibia. It is also possible for alternate embodiments of this invention to use a porous tibial plate. FIG. 27 shows protective foam being removed from the proximal surface of the non-porous tibial base plate. An insert trial may be placed onto the actual tibial base plate before impacting the femoral component onto the distal femur in order to protect the proximal surface of the plate.

Figure 28:
Figure 29A:
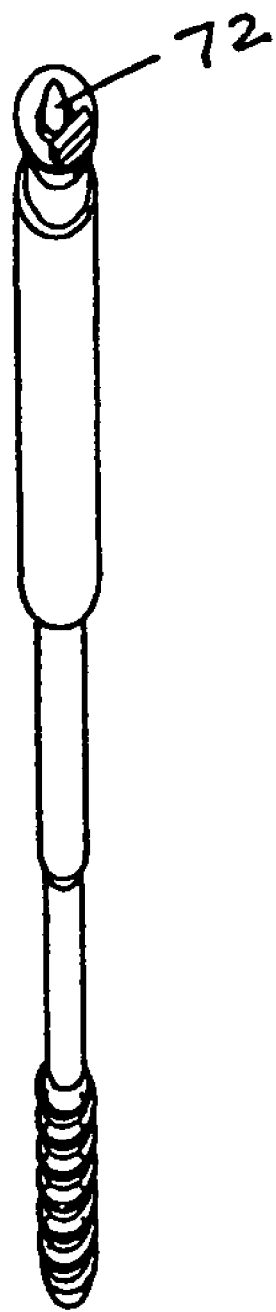
FIG. 29a is a perspective view of an alternate embodiment of an intermediate stem trial that uses a hole and detent mechanism to secure the intermediate trial stem to the plate trial.
Figure 29B:
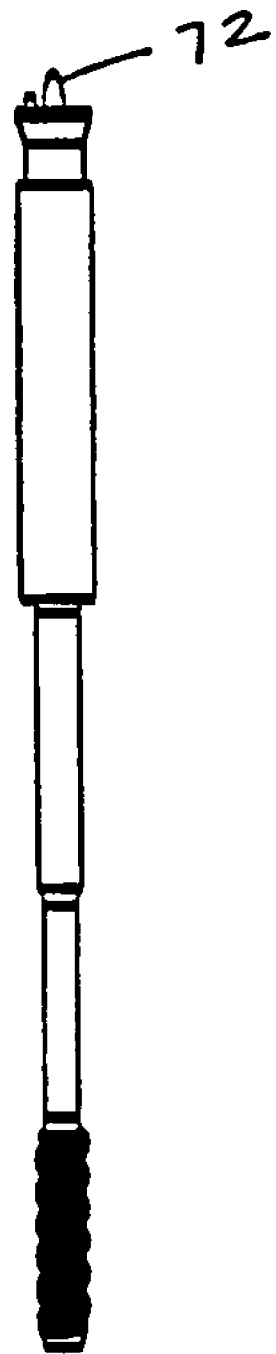

FIG. 28 shows the actual insert being placed on the tibial base plate and secured using the rotation peg with a torque wrench. In the preferred embodiment, approximately 75 inch pounds of torque is used to secure the rotation peg, but that may vary depending upon the prescribed clinical technique.

FIG. 8 shows an intermediate stem trial 32 according to the present invention being positioned on a plate trial 10 for revision surgery or other surgery where a long stem trial is needed. FIG. 9 shows the stem trial 52 being connected to the intermediate stem trial 32. This tibial trial so assembled as shown in FIGS. 8 and 9 is then used as shown beginning with FIG. 15 above.

After the implant components have been properly placed in the patient, knee structure is repositioned and the surgery completed.

Further non-limiting examples of possible embodiments for the coupling of the plate trial and the intermediate stem trial are depicted in FIGS. 29–37. FIGS. 29a and 29b show an embodiment of an intermediate stem trial that has a hole and detent mechanism 72 located at its proximal surface. The ball bearing or plunger 72 secures the intermediate stem trial in a proper anterior-posterior position of in lieu of using a threaded collar. The plate trial for use in combination with this embodiment has a small recess on its distal surface configured to receive the detent mechanism and hold it in place.

Figure 30A:
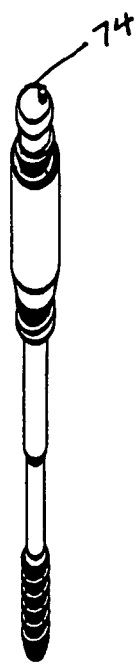
FIG. 30a is a perspective view of an alternate embodiment of an intermediate stem trial that has a half-round connecting portion.
Figure 30B:
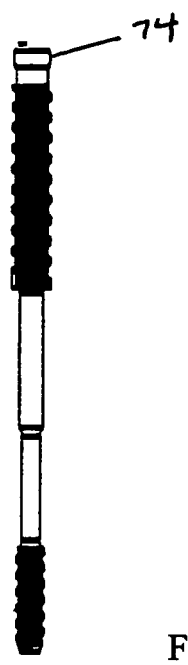
Figure 31:
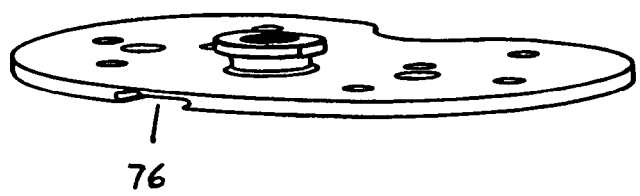
FIG. 31 is an anterior perspective view of a plate trial having a half-round mating groove for use with the intermediate stem trial of FIGS. 30a and 30b.
Figure 32:
FIG. 32 is an anterior elevation view of the plate trial of FIG. 31.

FIGS. 30a and 30b show an alternate embodiment of an intermediate stem trial that has a half-round connecting portion 74 located on its proximal surface. This half-round connecting portion 74 mates with a corresponding plate trial that has a half-round mating groove 76 on its distal surface, shown in FIGS. 31 and 32.

An additional embodiment of an intermediate trial stem is shown in FIGS. 33a and 33b. This embodiment features a T-slot connecting portion 78 on its proximal surface that mates with a T-slot mating groove 80 on the distal surface of a corresponding plate trial, shown in FIGS. 34 and 35.

Figure 36:
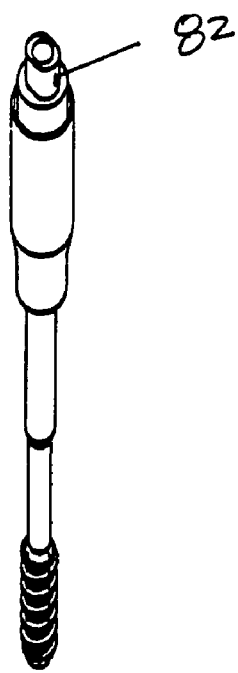
FIG. 36 is a perspective view of an alternate embodiment of an intermediate stem trial having a spring action collar that allows it to mate with a slotless plate trial.
Figure 37:
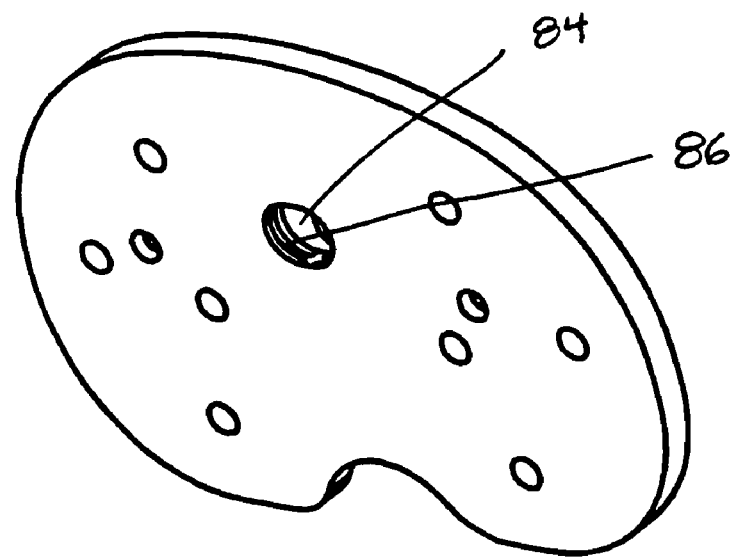
FIG. 37 is a perspective view of a slotless plate trial for use with the intermediate stem trial of FIG. 36.

FIG. 36 shows an intermediate trial stem that attaches to a plate trial without requiring a slot or mating groove. Instead of a flange, the intermediate trial stem has a connecting portion that comprises a spring action collar 82 on its proximal surface. The spring action collar 82 releases and locks with a ball detent mechanism 86 located within a recess on a corresponding plate trial. This corresponding plate trial does not necessarily feature a slot or mating groove, but has an opening 84 with a ball detent mechanism 86 within the recess of the opening 84 to secure the spring action collar 82 of the intermediate trial stem.

The disclosure of devices and processes as recited above is not intended to limit the scope of the present invention. It provides more broadly for an adapter to fit to the bottom or distal surface of a tibial or other trial without the need for retaining components to be inserted through the opposite surface. Various sizes and geometries of adapters may be used, and they may connect to various sizes and geometries of stems as necessary in order to offer any desired range of modularity. Such trials may be used for implantation of porous or non-porous coated implants, tibial prostheses with or without mobile bearings or fins, and with any desired structure or in any desired setting.

Having thus described various and preferred embodiments of apparatus, kits and methods for prosthetic implants, it should be apparent to those skilled in the art that certain advantages have been achieved. It should also be appreciated that various modifications, adaptations, and alternative embodiments thereof, may be made within the scope and spirit of the present invention. The invention is further defined by the following claims:

What is claimed is:

1. A prosthetic trial apparatus for use in preparing a patient for an implant, the trial apparatus comprising:
   (a) a plate having a top surface, a bottom surface, and a plate interface, the plate interface disposed between the top surface and the bottom surface; and
   (b) a trial adapter having a proximal end and a distal end and having
      (i) a first adapter interface at its proximal end:
         (1) wherein the first adapter interface is connected to the plate interface at the bottom surface of the plate in a removable manner; and
         (2) wherein the first adapter interface does not interfere with the top surface of the plate; and
      (ii) a second adapter interface at its distal end.

2. The prosthetic trial apparatus of claim 1, further comprising a trial stem having a proximal and a distal end, the distal end adapted to be inserted into the intramedullary canal of a patient's bone and the proximal end adapted to connect to the second adapter interface.

3. The prosthetic trial apparatus of claim 2, wherein the second adapter interface is a threaded surface and the trial stem has a threaded bore to receive the threaded surface.

4. The prosthetic trial apparatus of claim 1, wherein the plate interface is a cavity, and the first adapter interface fits into the cavity.

5. A tibial trial apparatus for use in preparing a patient for an implant, the tibial trial apparatus comprising:
   (a) a tibial trial plate having a top surface, a bottom surface, and a plate interface disposed between the top surface and the bottom surface; and
   (b) a trial adapter having a proximal end and a distal end and having
      (i) a first adapter interface at its proximal end:
         (1) wherein the first adapter interface is connected to the plate interface at the bottom surface of the plate in a removable manner; and
         (2) wherein the first adapter interface does not interfere with the top surface of the plate; and
      (ii) a second adapter interface at its distal end.

6. The tibial trial apparatus of claim 5, further comprising a trial stem having a proximal end and a distal end, the distal end adapted to be inserted into the intramedullary canal of a patient's tibia and the proximal end adapted to connect to the second adapter interface.

7. The tibial trial apparatus of claim 6, wherein the second adapter interface is a threaded surface and the trial stem has a threaded bore which cooperates with the threaded surface.

8. The tibial trial apparatus of claim 5, wherein the plate interface is a cavity, and the first adapter interface fits into the cavity.

9. The tibial trial apparatus of claim 8, wherein the plate interface is a dovetail slot and the first adapter interface is a chamfered flange adapted to be received by the dovetail slot.

10. The tibial trial apparatus of claim 9, wherein the chamfered flange has two edges and a surface having a boss, and the dovetail slot has an alignment groove, wherein the alignment groove is adapted to receive the boss to provide a secure connection between the tibial trial plate and the trial adapter.

11. The tibial trial apparatus of claim 10, wherein the adapter has an upper portion having a first longitudinal axis and a lower portion having a second longitudinal axis, providing an angled adapter, and wherein the boss orients the adapter about the first longitudinal axis relative to the tibial trial plate to direct the second longitudinal axis in the desired direction.

12. The tibial trial apparatus of claim 5, wherein the plate interface is a recess adapted to receive a detent mechanism, and the first adapter interface is a ball, plunger, or spring action collar that fits into the recess.

13. The tibial trial apparatus of claim 5, wherein the plate interface is a half-round mating groove, and the first adapter interface is a half-round connecting portion that fits into the groove.

14. The tibial trial apparatus of claim 5, wherein the plate interface is a T-slot mating groove, and the first adapter interface has a T-slot connecting portion that fits into the groove.

15. The tibial trial apparatus of claim 5, wherein tibial trial plate has an edge and the cavity extends from the edge of the plate to an appropriate location on the bottom surface of the plate.

16. The tibial trial apparatus of claim 5, wherein the tibial trial plate is a generally flat plate with a peripheral shape that corresponds to a tibial plate implant.

17. The tibial trial apparatus of claim 5, wherein the tibial trial plate corresponds to prosthesis implant plates for use with a mobile bearing knee.

18. The tibial trial apparatus of claim 5, wherein the tibial trial plate corresponds to prosthesis implant plates not for use with a mobile bearing knee.

19. The tibial trial apparatus of claim 5, further comprising an additional structure to secure the trial adapter to the tibial trial plate.

20. The tibial trial apparatus of claim 19, wherein the adapter has a threaded surface near its proximal end, and wherein the additional structure is a collar which cooperates with threaded surface of the adapter to allow tightening of the collar against the bottom surface of the plate.

21. The tibial trial apparatus of claim 20, further comprising a stopping mechanism to prevent the collar from becoming separate from the trial adaptor.

22. The tibial trial apparatus of claim 5, further comprising a trial stem adapted to be connected to the second adapter interface, wherein the trial adapter is configured with an angle to cause the trial stem to project at an angle other than 90 degrees relative to the bottom surface of the plate.

23. The tibial trial apparatus of claim 22, wherein the angle is in the posterior direction.

24. The tibial trial apparatus of claim 22, wherein the angle corresponds to an angle in the implant stem.

25. The tibial trial apparatus of claim 22, wherein the adapter has an upper portion having a first longitudinal axis and a lower portion having a second longitudinal axis, providing an angle is about 3 degrees to about 10 degrees.

26. The tibial trial apparatus of claim 5, wherein the tibial trial plate corresponds to a prosthesis implant with a porous surface.

27. The tibial trial apparatus of claim 5, wherein the tibial trial plate corresponds to a prosthesis implant without a porous surface.

28. The tibial trial apparatus of claim 5, further comprising a plurality of holes or openings in the tibial trial plate which are used to guide a punch or drill which prepares the proximal tibia for implantation of tibial plate pins, wherein at least one of the holes is counter-bored to a depth allowing headed pins to be recessed below the top surface of the plate without impinging upon or interfering with the top surface.

29. The tibial trial apparatus of claim 5, further comprising integral spikes on the bottom surface of the tibial trial plate to secure the position of the tibial plate trial until headed pins are inserted.

30. The tibial trial apparatus of claim 5, further comprising a T-post on the top surface of the tibial trial plate having an internal thread to accept a trial rotation peg and a flange to accept a trial mobile bearing insert.

31. The tibial trial apparatus of claim 28, wherein at least two of the plurality of holes or openings are coincident with distal spikes of a punch guide.

32. A tibial trial prosthesis, comprising:
(a) a tibial trial plate having first side, a second side, and a plate interface disposed between the first and second sides; and
(b) an intermediate stem trial having first and second ends, the first end adapted to connect to the plate interface at the first side of the tibial trial plate:
  (1) wherein the first end is connected to the tibial trial plate first side in a removable manner; and
  (2) wherein the first end does not interfere with the second side of the plate.

33. The tibial trial prosthesis of claim 32, further comprising a trial stem having a proximal and a distal end, the distal end adapted to be inserted into the intramedullary canal of a patient's bone and the proximal end adapted to connect to the second end of the intermediate trial stem.

34. A tibial trial prosthesis kit for replacement of the knee joint, comprising:
(a) a plurality of tibial trial plates having a range of shapes or sizes or both, each plate having a top surface, a bottom surface, and a plate interface disposed between the top surface and the bottom surface;
(b) a plurality of trial stems having a range of various lengths, angles, and widths, each trial stem adapted to be inserted into the intramedullary canal of a patient's bone; and
(c) a plurality of adapters having a range of various angles to fit range of plates for various geometries and modularity, each adapter having a proximal end and a distal end and including:
  (i) a first adapter interface at its proximal end:
    (1) wherein the first adapter interface is connected to the plate interface at the bottom surface of the tibial trial plate in a removable manner; and
    (2) wherein the first adapter interface does not interfere with the top surface of the plate; and
  (ii) a second adapter interface at its distal end adapted to connect to the trial stem.

35. The tibial trial prosthesis kit of claim 34, wherein at least one of the plurality of adapters has an upper portion having a first longitudinal axis and a lower portion having a second longitudinal axis, and wherein the first longitudinal axis and second longitudinal axis are oriented to provide an adapter having an angle from about zero degrees to about ten degrees.

36. The tibial trial prosthesis kit of claim 34, wherein the plate interface comprises a cavity, into which the first adapter interface fits.

37. The tibial trial prosthesis kit of claim 34, wherein the second adapter interface is threaded and wherein the trial stem has a threaded bore which secures onto the threaded portion of the second adapter interface.

38. A method of replacing a knee joint in a patient, comprising:
(a) resecting the proximal end of the tibia to expose the intramedullary canal of the tibia;
(b) inserting and trialing various trial implant components to determine which trial implant corresponds as nearly as possible to the geometry of the resected proximal end of the tibia and provides the desired angle of inclination of the plate relative to the stem, the trial implant components comprising:

(i) one or more plates having a top surface, a bottom surface, and a plate interface disposed between the top surface and the bottom surface;
(ii) one or more stems; and
(iii) one or more adapters for connecting a stem to a plate, having a proximal end and a distal end and including:
　(1) a first adapter interface at the proximal end: wherein the first adapter interface is adapted to connect to the plate interface at the bottom surface of the plate in a removable manner; and wherein the first adapter interface is adapted to connect to the plate interface without interfering with the top surface of the plate; and
　(2) a second adapter interface at its distal end adapted to connect to the stem; and
(c) selecting and inserting a tibial implant prosthesis corresponding as nearly as possible to the trial implant components.

\* \* \* \* \*